United States Patent [19]

Sawada et al.

[11] Patent Number: 5,234,904

[45] Date of Patent: Aug. 10, 1993

[54] ANTIHYPERTENSIVES CONTAINING POLYSACCHARIDE PEPTIDOGLYCAN COMPLEXES EXTRACTED FROM THE CELL WALL OF LACTIC ACID BACTERIA

[75] Inventors: Haruji Sawada; Masayoshi Furusiro; Kouichi Hirai; Mahoko Motoike; Tunekazu Watanabe; Teruo Yokokura; Masaaki Watanuki; Seizaburo Kobayashi, all of Tokyo, Japan

[73] Assignee: Kabushiki Kaisha Yakult Honsha, Tokyo, Japan

[21] Appl. No.: 542,734

[22] Filed: Jun. 22, 1990

[30] Foreign Application Priority Data

Jun. 26, 1989 [JP] Japan .................... 1-160851

[51] Int. Cl.$^5$ .................... A61K 37/02; C07K 15/04; C07K 15/14
[52] U.S. Cl. .................... 514/8; 426/656; 514/322; 514/395
[58] Field of Search .................... 514/8; 530/395, 322; 426/656

[56] References Cited

PUBLICATIONS

Journal of Antibiotics, Ser-A 20(6) 334-343 (1967), Arai et al.

Sawada, H. et al., *Agric. Biol. Chem.*, 54(12):3211-3219, Dec. 1990.
Koga, t. et al., *Molecular Immunology*, 16:153-162, 1979.
Kawasaki, A., *Chem. Abs.*, 98(3):394, No. 98:1521e, 1983.
Hamada, O. et al., *Chem. Abs.*, vol 71(1):945c, 1968.
Tipper, D. et al., *JBC.*, vol. 243 No. 11:3169-3179, 1968.
Campbell, J. et al., *Biochemistry*, 8(1):193-200, 1969.
Kushikata, *Chem. Abs.*, vol 68, (11):48112u, 1967.
Verhoef, J., et al., *Chem. Abs.*, vol. 101(21):189136s, 1983.
Verhoef, J., et al., *Chem. Abs.*, vol 103(23):191164; 1985.
Osol (Editor), Remington's Pharmaceutical Sciences, Mach Publishing Co., 1980.

*Primary Examiner*—Howard E. Schain
*Attorney, Agent, or Firm*—Michael N. Meller

[57] ABSTRACT

The present invention relates to antihypertensives and food and drinks, containing as effective component polysaccharideglycopeptide complexes derived from cell wall of Gram positive bacteria (also referred to as peptidoglycan). The present invention provides extremely strong and safe antihypertensives and food and drinks, which may exert hypotensive effects if administered orally to spontaneous hypertensive rats and renal hypertensive rats at a single dose as low as 1 mg/kg.

2 Claims, 6 Drawing Sheets

○ Muramic acid concentration ($\mu$mole / ml)

● Concentration of polysaccharide - glycopeptide complex (mg / ml)

ANTIHYPERTENSIVES CONTAINING POLYSACCHARIDE PEPTIDOGLYCAN COMPLEXES EXTRACTED FROM THE CELL WALL OF LACTIC ACID BACTERIA

BACKGROUND OF THE INVENTION

1. Field of the Invention

The present invention relates to antihypertensives and food and drinks, containing as an effective component, polysaccharide-peptidoglycan complexes derived from the cell wall of Gram positive bacteria.

2. Description of the Prior Art

It is reported that the recent incidence of essential hypertension with its etiology being unknown has reached 90% of the total incidence of hypertension and that the remaining 10% is included in secondary hypertension concomitantly developed along with renal, adrenal or nervous disorders.

Hypertension, if untreated, induces cardiovascular disorders, so that a variety of research institutes have been engaged in developing the agents for preventing or therapeutically treating the disorders, as the most important research subject.

Antihypertensives which have already been developed and introduced into market are classified according to the action mechanism, as follows;

1. Sodium-reabsorption suppressing diuretics working in uriniferous tubule; Hypotensive diuretics such as thiazide, etc.
2. Noradrenaline (NA) depleting agent; Rauwolfia alkaloid, etc.
3. Peripheral vasodilators; hydralazine, etc.
4. Stimulators of adrenaline receptors; methyldopa, etc.
5. Peripheral sympatholytic agents and central sympatholytic agents; guanethidine, etc. and clonidine, etc.
6. β-receptor-blockers; propranolol, etc.
7. Angiotensin-converting-enzyme (ATC) inhibitor; Captopril, etc.
8. Others.

Further research to develop a variety of such agents has been vigorously carried out currently.

These antihypertensive agents, which generally are administered continuously for a long period, have a profound pharmacological efficacy along with a lot of side effects. Therefore, there is a need for agents which may be administered more safely.

Alternatively, it has been known that the action to suppress blood pressure increase is found in some substances from natural origin including polysaccharides produced by plant, sea weeds and microorganisms, such as pectinate (Japanese Patent Laid-open 112520/1988), alginic acid (Japanese Patent Laid-open 143559/1984), potassium alginate (Japanese Patent Laid-open 34853/1984), calcium alginate (Japanese Patent Laid-open 130523/1985), mannans (Japanese Patent Laid-open 101327/1988), a high-molecular polysaccharide MPS-80 produced by lactic acid bacterium (Japanese Patent Laid-open 19092/1984).

It has been also reported in the academic society that besides those described above, heparin, carrageenan, dextran, cellulose or polydextrose or the like has also the action to suppress blood pressure increase or to decrease blood pressure.

SUMMARY OF THE INVENTION

However, these substances have disadvantages in that all of the substances should be administered orally in large amounts in order to exert their hypotensive action.

The present inventors have carried out intensive research in order to develop safer agents which can exhibit profound antihypertensive action even through their oral administration. Consequently, they have found out that the polysaccharidepeptidoglycan complexes known as the cell wall component of certain Gram positive bacteria such as lactic acid bacterium, Lactobacillus, Bifidobacterium, Streptococcus, etc. exhibit strong antihypertensive action. Thus, they have accomplished the present invention.

The present invention relates to antihypertensives and food and drinks, containing, as effective component, polysaccharidepeptidoglycan complexes, the cell wall component of Gram positive bacteria. The present invention provides antihypertensives and food and drinks containing them, which may be administered orally to spontaneous hypertensive rats and renal hypertensive rats at a single dose as small as 1 mg/kg to exert extremely strong hypotensive effects in such a safe manner.

The antihypertensives and food and drinks containing them of the present invention are those containing the polysaccharide-peptidoglycan complexes derived from the cell wall of Gram positive bacteria.

Any polysaccharide-peptidoglycan complexes derived from the cell wall of Gram positive bacteria may be used in the present invention. In view of safety, the polysaccharide-peptidoglycan complexes from lactic acid bacteria such as Lactobacillus or Bifidobacterium may be preferable.

The surface layer of the cell wall of lactic acid bacterium mainly consists of a layer composed of peptidoglycan, and teichoic acid and polysaccharides are present on its outer layer.

The peptidoglycan has a basic unit of the disaccharide consisting of N-acetylglucosamine linked to N-acetylmuramic acid, the two substances being substituted with the peptide chains of 4 to 5 amino acids. The basic units are cross-linked with each other through amino acids and peptides into a macromolecule. In the cell wall, the basic unit is linked with teichoic acid and polysaccharide through a phosphate diester-bond. The representative examples are as follows;

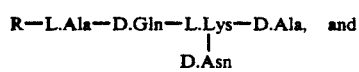

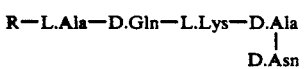

wherein each abbreviation in the formulae means the following amino acids, respectively, L-Ala is L-alanine D-Gln is D-glutamine L-Lys is L-lysine -continued D-Asn is D-asparagine and R is polysaccharide

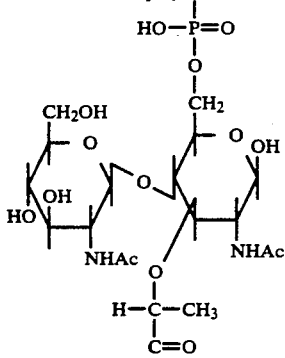

The basic unit is shown in the above formulae, but a certain preparative method for polysaccharide-peptidoglycan complexes (for example, hot-water extraction, autolysis) may produce complicated compounds where N-acetylglucosamine is linked to the muramic acid molecule in the formula R.

A mixture comprising such complicated compounds may be also the polysaccharide-peptidoglycan complex constituting the antihypertensives of the present invention.

On the other hand, it has been currently reported that lactic acid bacterium has a lot of physiological actions. That is, antitumor action was reported by I. Kato et al., Gann, 72, 517 (1981), and N. Yasutake et al., Med. Microbiol. Immunol., 173, 113 (1984); anti-infectious action, by K. Nomoto et al., J. Clin. Immunol., 17, 91 (1985); macrophage activation, by I. Kato et al., Microbiol. Immunol., 27, 611 (1983); activation of natural killer cells, by I. Kato et al., Microbiol. Immunol., 27, 209 (1984). The polysaccharide-peptidoglycan complexes from lactic acid bacterium have been reported to have antitumor action (Japanese Patent Laid-open 196521/1988) and macrophage activation effect (Japanese Patent Laid-open 126827/1988). However, the fact that the polysaccharide-peptidoglycan complexes from lactic acid bacterium have hypotensive action, has never been demonstrated.

The method for preparing an antihypertensive agent according to the present invention will now be explained. The polysaccharide-peptidoglycan complexes to be used in the present invention may be obtained from a variety of Gram positive bacteria following known methods. The sugar composition and amino acid sequence of the complexes more or less depends on a species of lactic acid bacterium. For example, all of the complexes obtained from various Lactobacillus strains, including Lactobacillus casei (Lactobacillus is referred to as L. hereinafter), L. acidophilus, L. alimentarius, L. amylovorus, L. bifermentans, L. brevis, L. buchneri, L. collinoides, L. coryneformis, L. crispatus, L. curuvatus, L. delbrueckii, L. helveticus, L. jensenii, L. lactis, L. murinus, L. sake, L. salivarius, etc. have the aforementioned amino acid sequences and may be preferable as the polysaccharide-glycopeptide complexes constituting antihypertensives of the present invention.

The method for producing the polysaccharide-peptidoglycan complexes as the effective component of the antihypertensives of the present invention, using lactic acid bacterium, will now be described in more detail.

Various species of lactic acid bacterium as the material are cultured via the culture conditions suitable for the microbiological properties of each species, to collect the cultured bacterial cells. These may be cultured in the culture medium routinely used for lactic acid bacterium, for example, Rogosa medium, but a complex medium using corn steep liquor or distiller's soluble, etc. as nitrogen source may be also used. The culture method may follow the routine method for lactic acid bacterium. In order to extract the polysaccharide-peptidoglycan complexes from the cultured bacterial cells, hot-water extraction, autolysis, or enzyme degradation using cell-wall lytic enzymes may be employed.

The polysaccharide-peptidoglycan complexes may be extracted by hot-water extraction in such manner that the bacterial cells at a concentration of about 10–80 mg/ml are suspended in hot water at 50°–100° C. for extraction for approximately 10–60 minutes. Preferably, the extraction may be carried out at 100° C. for 30 minutes. It is not necessary to adjust the a pH of specifically, but pH 6–8 may be preferable, generally. In order to autolyze the bacterium to extract polysaccharide-peptidoglycan complexes, the bacterial cells at a concentration of about 10–80 mg/ml are suspended in hot water at 50°–60° C., followed by autolysis at a pH of 6–8 for about 1 to 5 hours, and treated under heating at 100° C. for 5 to 30 minutes. Preferable conditions are a is 2-hour autolysis at 55° C. and extraction under heating at 100° C. for 10 minutes. In order to treat the bacterial cells enzymatically to extract polysaccharide-peptidoglycan complexes, lysozyme, N-acetylmuramidase, N-acetylglucosamidase, etc. may be reacted with the bacterial cells for an appropriate time to cleave the basal membrane structure of the cell wall thereof to extract polysaccharide-peptidoglycan complexes.

The polysaccharide-peptidoglycan complexes extracted in such a manner may be purified according to routine methods. More specifically, the protein which exists in a large amount in the crude-extract is removed by 5% perchloric acid or trichloroacetic acid or the like. Subsequently, the resulting solution is applied to an anion-exchange column to remove protein and high-molecular nucleic acids. The remaining protein and nucleic acids are further decomposed by protease and nuclease, respectively, and the enzymes used may be removed by passing them through a column packed with resin for hydrophobic chromatography. In such a manner, a sample from which nearly all of the protein and high-molecular nucleic acids present are removed is dialyzed against distilled water, using a dialyzing membrane having a fractionated molecular weight of 50,000. When further purification is needed, the dialysate may be passed through activated charcoal and the eluate may be freeze-dried.

The polysaccharide-peptidoglycan complexes purified by the aforementioned method may be fractionated by gel chromatography, if necessary.

The antihypertensives containing as effective component the polysaccharide-peptidoglycan complexes of the present invention may be administered orally, intraperitoneally or intraveneously. Oral administration thereof may be preferable in order to exert its hypotensive effects efficiently. They may be administered at a single dose as low as 1–5 mg/kg. Subsequently, about 2 to 3 hours after the administration, the hypotensive effect over 10 to 30 mmHg may be thereby observed and last more than 12 to 24 hours. The continuous administration thereof may be still more effective and in that case, even a lesser dose may produce hypotensive effect.

The antihypertensives of the present invention have the following excellent characteristic features;
1. They are the antihypertensives originated from lactic acid bacteria, which are used in the yogurt production.
2. They are the substances from natural origin which can exhibit hypotensive effects at a dose much less than the dose of the known polysaccharides produced by plants, sea weeds and microorganisms.
3. Since they are water soluble, they can be readily prepared in appropriate formulations.

In addition, they are extremely safe even if they are administered continuously for a long period.

DESCRIPTION OF THE PREFERRED EMBODIMENTS

1. Production embodiments

Figure 1:
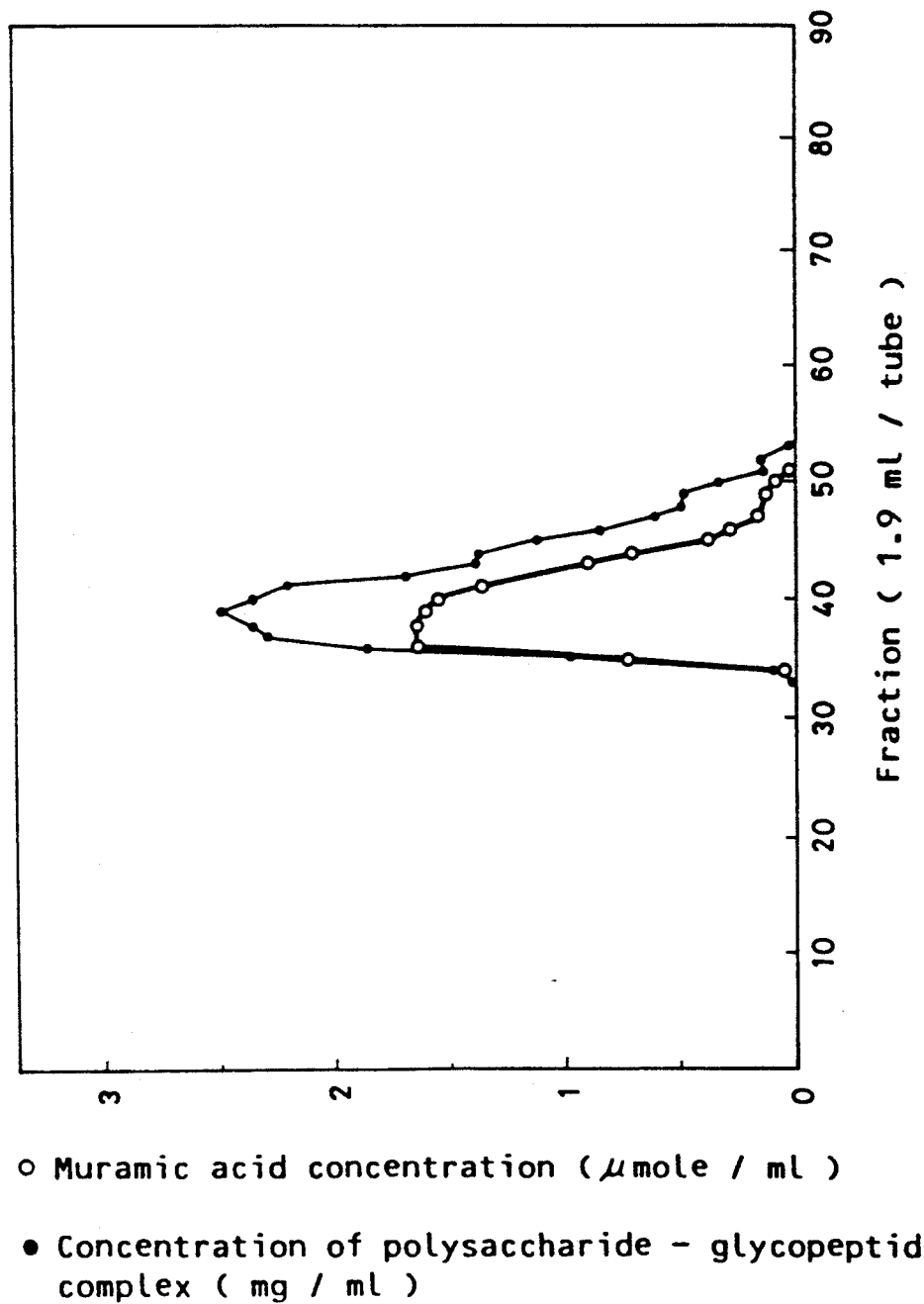
FIG. 1 is a diagram showing the result of gel filtration chromatography on a Sephacryl S-300 column of polysaccharide-peptidoglycan complexes.

Specific production embodiments are now described hereinafter.

Production Example 1

In 400 l of corn steep liquor medium (4% glucose, 14% corn steep liquor, 0.1% monopotassium phosphate, 0.1% dipotassium phosphate) was inoculated Lactobacillus casei YIT9018 and cultured at 35° C. for 20 hours, keeping the pH at 6 using sodium hydroxide. After the completion of the culture, the culture medium was centrifuged at 10,000 rpm for 5 min. to produce bacterial cells of a 1.3 kg dry weight after washing. These are autolyzed at 55° C. and pH 7 for 2 hours and extracted under heating at 100° C. for 10 min., to produce the extract LEx of 234 g. To 100 g of the extract LEx was added 5 l of 5% perchloric acid, and the precipitated protein and the like were removed by centrifuge at 14,000 rpm for 10 minutes. The precipitated substance was suspended in 1 l of distilled water, and then the resulting suspension was adjusted to pH 8.5 with 25% aqueous ammonia for dissolving the suspension, and then perchloric acid was added again to a final concentration of 5% followed by washing. The supernatant was collected and dialyzed against distilled water. The dialysate was passed through a Q-Sepharose-First-Flow column for adsorbing nucleic acids and protein, followed by concentration and drying by a rotary evaporator. To the residue was added 200 ml of 0.1M acetate buffer (pH 5.4) containing 0.1 mM zinc chloride for dissolution, and then 10 mg of nuclease P1 (manufactured by Yamasa, Co.; Cord No. 7801) was added to the resulting solution to degrade the remaining high-molecular nucleic acids at 50° C. for 5 hours. Subsequently, 10 mg of trypsin (manufactured by Sigma, Co; Type XIII) was added to degrade the remaining protein at 37° C. for 6 hours. The solution was passed through a Phenyl Sepharose Cl-4B column to remove the remaining protein and colored components. The resulting solution was dialyzed against distilled water, using a dialyzing membrane of a 50,000 fractionated MW (manufactured by Spectra Co.; Spectra/pore 6) and the dialysate was lyophilized to obtain 3,340 mg of polysaccharide-glycopeptide complexes (SG-1) in white fiber.

Production Example 2

To 4 l of Rogosa medium (2% glucose, 1% trypticase pepton, 0.5% yeast extract, 0.3% tryptose, 0.3% monopotassium phosphate, 0.3% dipotassium phosphate, 0.17% sodium acetate trihydrate, 0.02% 1-cysteine sulfate, 0.1% Tween 80, and a trace amount of metal salt including magnesium sulfate, iron sulfate and manganese sulfate) was inoculated Lactobacillus casei YIT9018 and cultured initially at pH 6.8 and 35° C. for 20 hours, followed by centrifuge at 10,000 rpm for 5 min, to produce the washed bacterial cells which weight was 8 g if converted into dry weight. These cells were heated and extracted at a pH of 7 and 100° C. for 30 minutes to produce a crude extract of 1,320 mg. To the crude extract was added 100 ml of 5% perchloric acid and the precipitated protein and the like were removed by centrifuging at 14,000 rpm for 10 minutes. The precipitated substance was suspended in 50 ml of distilled water, and the resulting suspension was then adjusted to a pH of 8.5 with 25% aqueous ammonia for dissolution. Perchloric acid was added again to a final concentration of 5% followed by washing. The supernatant was collected and dialyzed against distilled water. The dialysate was passed through a Q-Sepharose-First-Flow column for adsorbing nucleic acids and protein, followed by concentration and drying by a rotary evaporator. To the residue was added 50 ml of 0.1 mM acetate buffer (pH 5.4) containing 0.1 mM zinc chloride for dissolution, and then 1 mg of nuclease P1 (manufactured by Yamasa, Co.; Cord No. 7801) was added to the resulting solution to degrade the remaining high-molecular nucleic acids at 50° C. for 5 hours. Subsequently, 1 mg of trypsin (manufactured by Sigma, Co; Type XIII) was added to degrade the remaining protein at 37° C. for 6 hours. The solution was passed through a Phenyl Sepharose CL-4B column to remove the remaining protein and colored components. The resulting solution was dialyzed against distilled water, using a dialyzing membrane of a 50,000 fractionated MW (manufactured by Spectra Co.; Spectra/pore 6) and the dialysate was lyophilized to obtain 48 mg of polysaccharide-peptidoglycan complexes (SG-1) in white fiber. 2. Physico-chemical properties Physico-chemical properties of the polysaccharide-peptidoglycan complexes obtained in Production Example 1 will now be explained.

(1) Molecular weight

FIG. 1 shows the results of gel filtration chromatography on a Sephacryl S-300 column.

The chromatography condition is as described in FIG. 1; column size, 1.6×90 cm; fraction size, 1.87 ml/tube; sample load, 50 mg; developer, 50 mM aqueous ammonium carbonate (pH not adjusted). The present substance was developed under the above conditions and eluted nearly at a void volume. On a basis of the eluted positions of the dextran standards having a variety of average molecular weights, the average molecular weight of the polysaccharide-peptidoglycan complexes was estimated about 180,000.

(2) Decomposition point

The present substance began to change color around 265° C. and turned black at 270° to 275° C.

(3) Ultraviolet absorption spectrum

Figure 2:
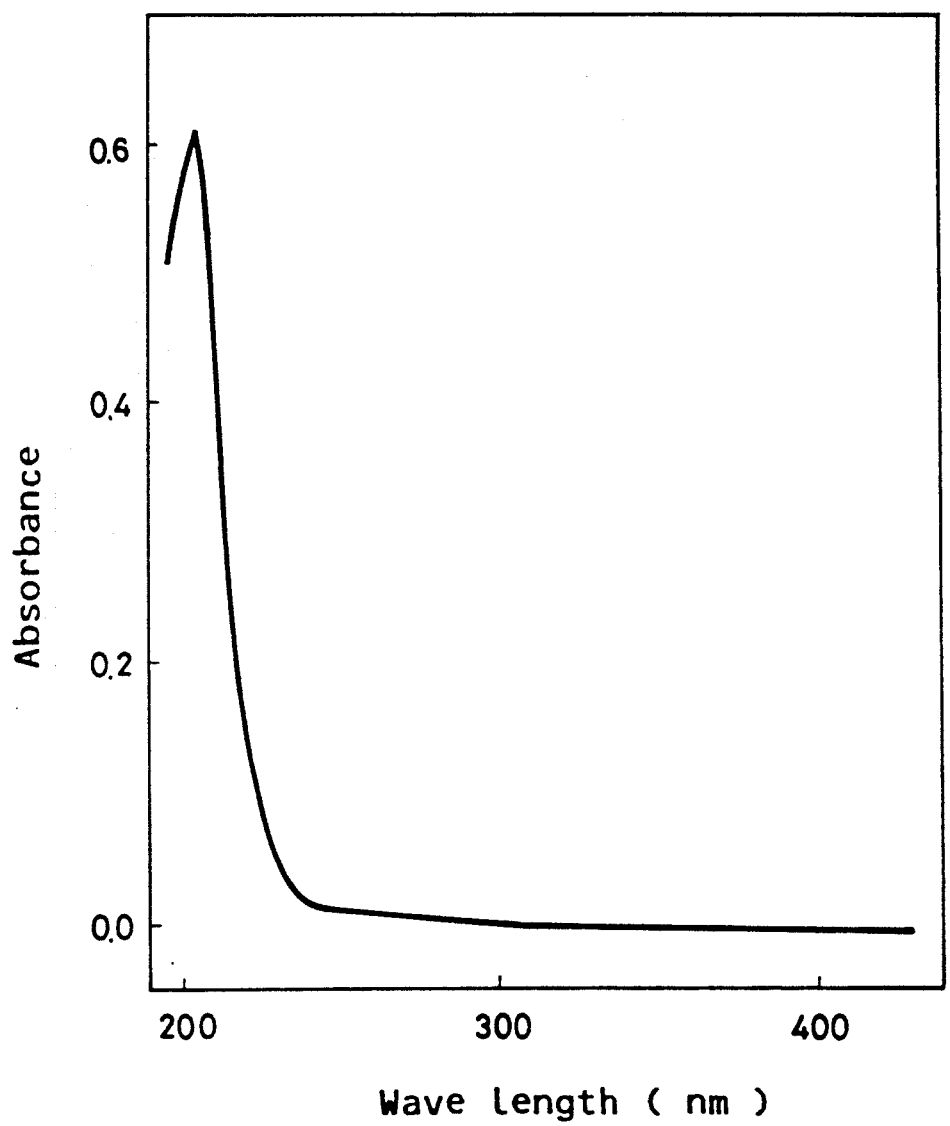
FIG. 2 shows an ultraviolet absorption spectrum of polysaccharide-peptidoglycan complexes.

FIG. 2 is an ultraviolet absorption spectrum of the polysaccharide-peptidoglycan complexes.

(4) Infrared absorption spectrum

Figure 3:
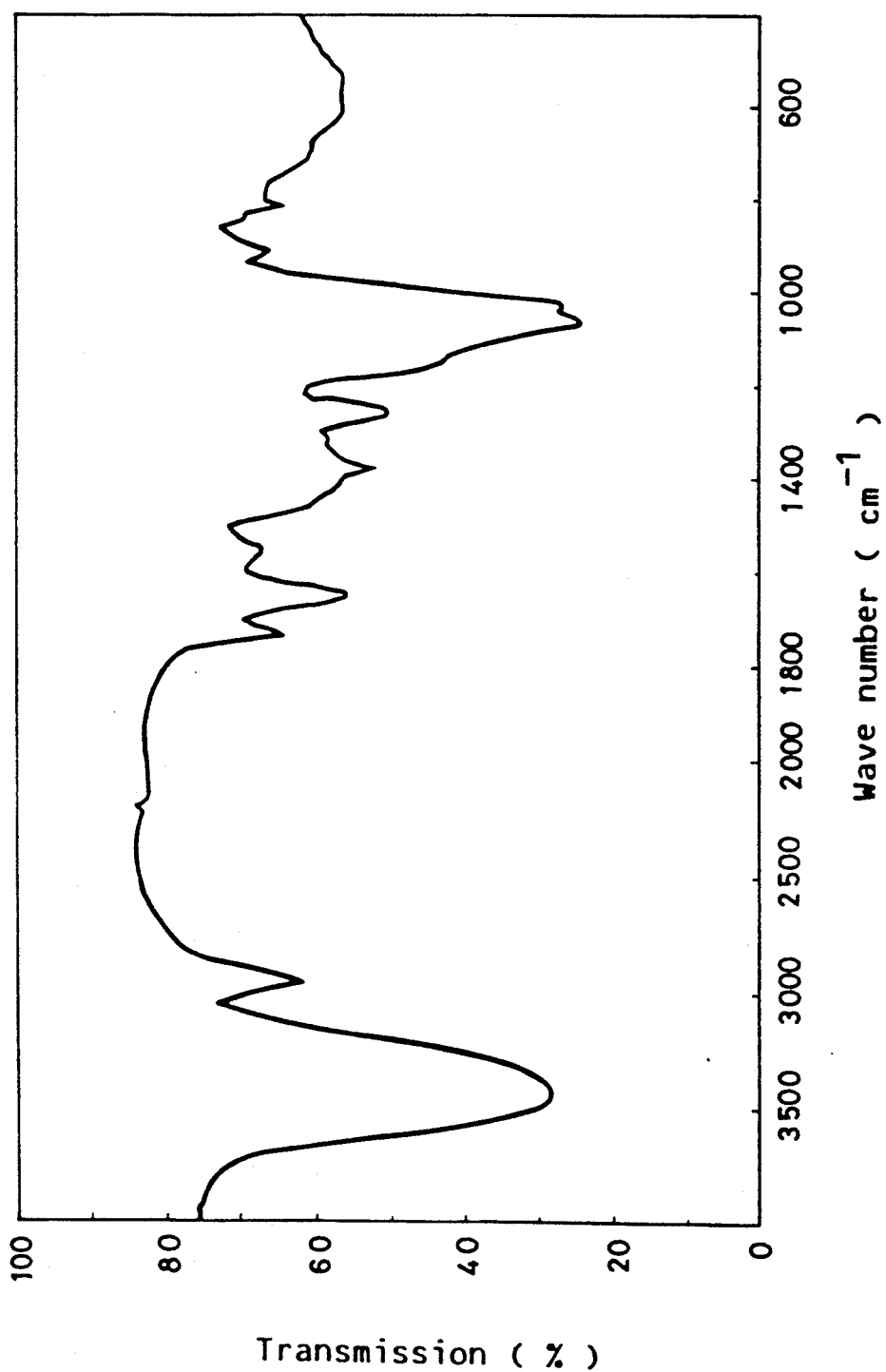
FIG. 3 shows an infrared absorption spectrum of polysaccharide-peptidoglycan complexes.

FIG. 3 is an infrared absorption spectrum of polysaccharide-peptidoglycan complexes.

(5) Solubility in solvents

The present substance is soluble in water, but insoluble in methanol, ethanol, acetone and ether.

| (6) Color reaction | |
| --- | --- |
| 1. Molisch reaction | positive |
| 2. Anthrone reaction | positive |
| 3. Orcinol reaction | positive |
| 4. Phenol-sulfuric acid reaction | positive |
| 5. Elson-Morgan reaction | positive |
| 6. Carbazole-sulfuric acid reaction | positive |
| 7. Aniline-hydrochloric acid reaction | negative |

(7) Identification of the solution's pH

The aqueous 0.1 to 0.5% solution of the present substance showed neutral pH.

(8) Color of the present substance

The lyophilized product of the present substance was white in the form of fibers.

(9) Types of constituting sugars

GLC on 5% SE-52 Bonded (capillary column of 0.25 mm inner diameter 25 m) was carried out to examine the constituting sugars of the polysaccharide-peptidoglycan complexes.

Condition; Temperature increase 130°–260° C. (4° C./min). A sample placed in a block heater was hydrolyzed in ZN trifluoroacetic acid under heating for 16 hours, followed by drying under reduced pressure. To the remaining residue was added a mixture of methanol, acetic anhydride and pyridine (500:50:10) in order to acetylate the aminosugar at 25° C. for 15 minutes, which was then trimethylsilylated to be subjected to GLC analysis. Consequently, it was determined that the present substance had the constituting sugars comprising glucose, galactose and rhamnose. An aminosugar, N-acetylgucosamine was also observed.

(10) Composition of constituting sugar

Table 1 shows the results of GLC analysis of a sample and the sugar content per g the polysaccharide-peptidoglycan complexes.

TABLE 1

| Constituting sugars | μmol/g |
| --- | --- |
| glucose | 2161 |

TABLE 1-continued

| Constituting sugars | μmol/g |
| --- | --- |
| rhamnose | 1503 |
| galactose | 694 |
| N-acetylglucosamine | 361 |
| N-acetylgalactosamine | — |

(11) Types of constituting amino acids

The constituting amino acid of the polysaccharide-glycopeptide complexes was analyzed by the following method.

A sample was degraded in boiling water with 4N hydrochloric acid for 6 hours, and then placed into an evaporator for concentration and drying, followed by addition of distilled water. Subsequently, the solution was again concentrated and dried. The above procedure was repeated three times, and then distilled water was added to a given concentration to be subjected to an amino acid sequencer for amino acid sequence analysis and quantitative determination. As a result, asparagine, glutamine, alanine and lysine were observed as the constituting amino acids of the present substance.

(12) Composition of constituting amino acids

Table 2 shows the results of amino acid analysis and the amino acid content per g the polysaccharide-peptidoglycan complexes.

TABLE 2

| Constituting amino acids | μmol/g |
| --- | --- |
| asparagine | 35.9 |
| glutamine | 6.0 |
| alanine | 4.1 |
| lysine | 1.5 |

(13) Constituting muramic acid content

The muramic acid content per g polysaccharide-peptidoglycan complexes was measured following the method described by Hadzija, Anal. Biochem., 60, 512, 1974, and it turned out to be 378 μmol. (14) $H^1$-NMR spectrum (in $D_2O$, TSP standard)

Figure 4:
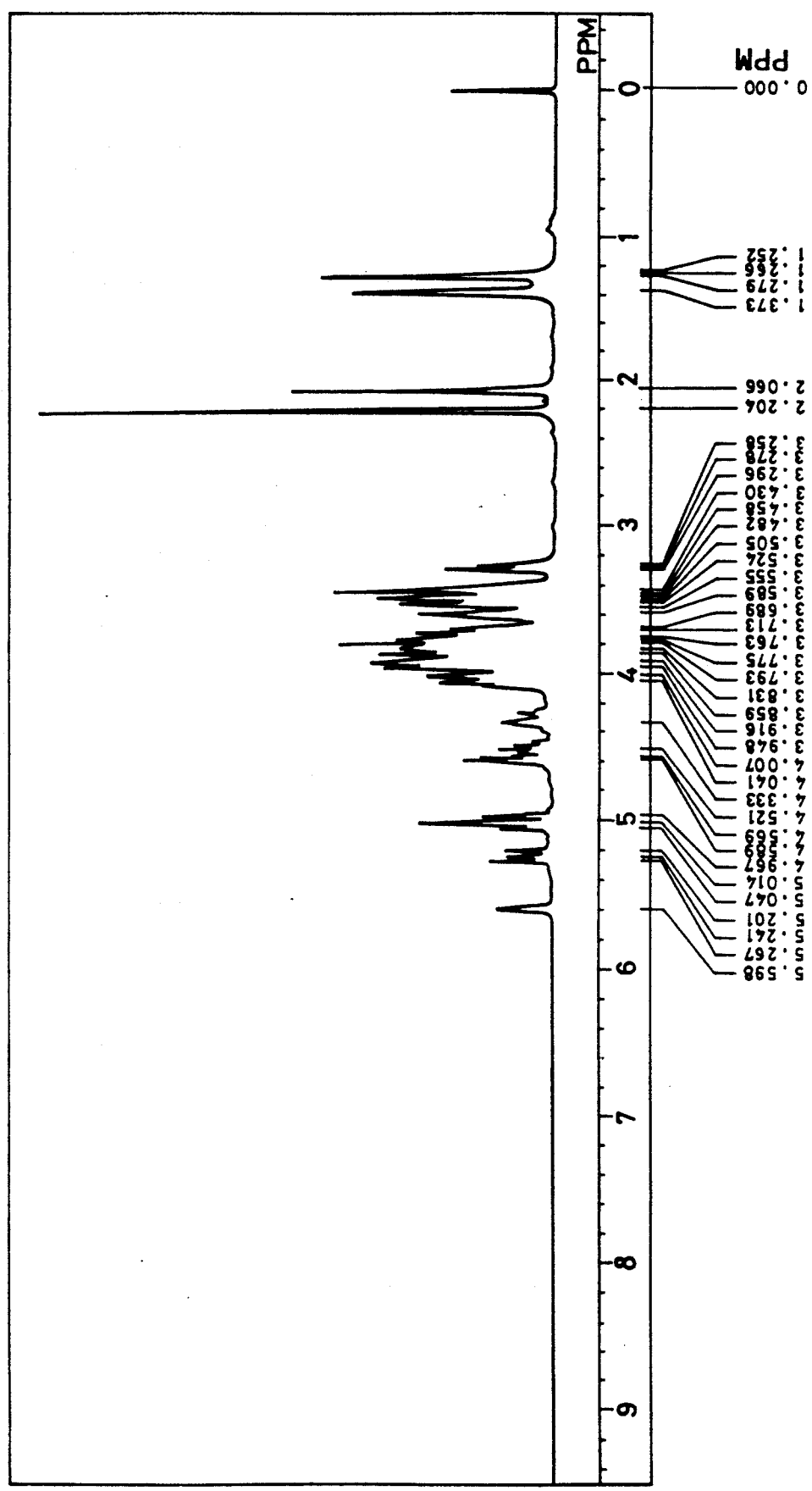
FIG. 4 shows an $H^1$- NMR spectrum of polysaccharide-peptidoglycan complexes.

FIG. 4 shows the $H^1$-NMR spectrum of the polysaccharide-peptidoglycan complexes.

(15) Enzymatic degradation

The present substance dissolved in 50 mM acetate buffer was treated with various types of enzymes. Enzymatic degradation was examined, using as an index the increase in the reduced sugar content by the Somogyi-Nelson method.

Enzyme used and reaction condition

1. α-amylase (Behringer, Co.); pH 5.9, 37° C., 5 hours
2. β-amylase (Behringer, Co.); pH 4.8, 30° C., 5 hours
3. amyloglycosidase (Behringer, Co.); pH 4.8, 30° C., 5 hours 4. α-galactosidase (Behringer, Co.); pH 4.8, 30° C., 5 hours
5. β-galactosidase (Behringer, Co.); pH 4.8, 30° C., 5 hours The increase in the reduced sugar content was not at all observed under all of the above conditions 1 to 5.

(16) $LD_{50}$

To male Balb/c mice of age 7 weeks, weighted about 25 g, were given different oral doses of a sample dissolved in distilled water, singly, and then they were kept under the observation for 10 days to determine $LD_{50}$. Consequently, even the mice under the regimen of a dose 2 g/kg or more did not die. Thus, $LD_{50}$ could not be determined.

3. Hypotensive action

EXAMPLE 1

Hypotensive action on spontaneous hypertensive rats (1) Method

Male spontaneous hypertensive rats (SHR), aged 17 weeks or more, which showed a systolic blood pressure (SBP) of 170 mmHg or more, were used in these animal experiments. Through a zonde, groups of 5 rats were given 1 mg/kg or 10 mg/kg of the polysaccharide-peptidoglycan complexes or 0.5 ml/100 g water (a control group), individually. For blood pressure measurement, rats unanesthetized were prewarmed at 38° C. for a few minutes to measure SBP at the caudal vein and the heart rate (HR), was determined using a programmable sphygmomanometer (PS-100 manufactured by Riken Kaihatu, K. K.). Measurement was carried out before and 3, 6, 12 and 24 hours after the sample administration.

The change in SBP or HR before and after the administration was determined (the average reduction±S.D.) and was statistically examined compared with those changes in the control group, using a Student's t-test. The change, if the risk level 5% or more was observed, was defined as significant.

(2) Results

Figure 5:
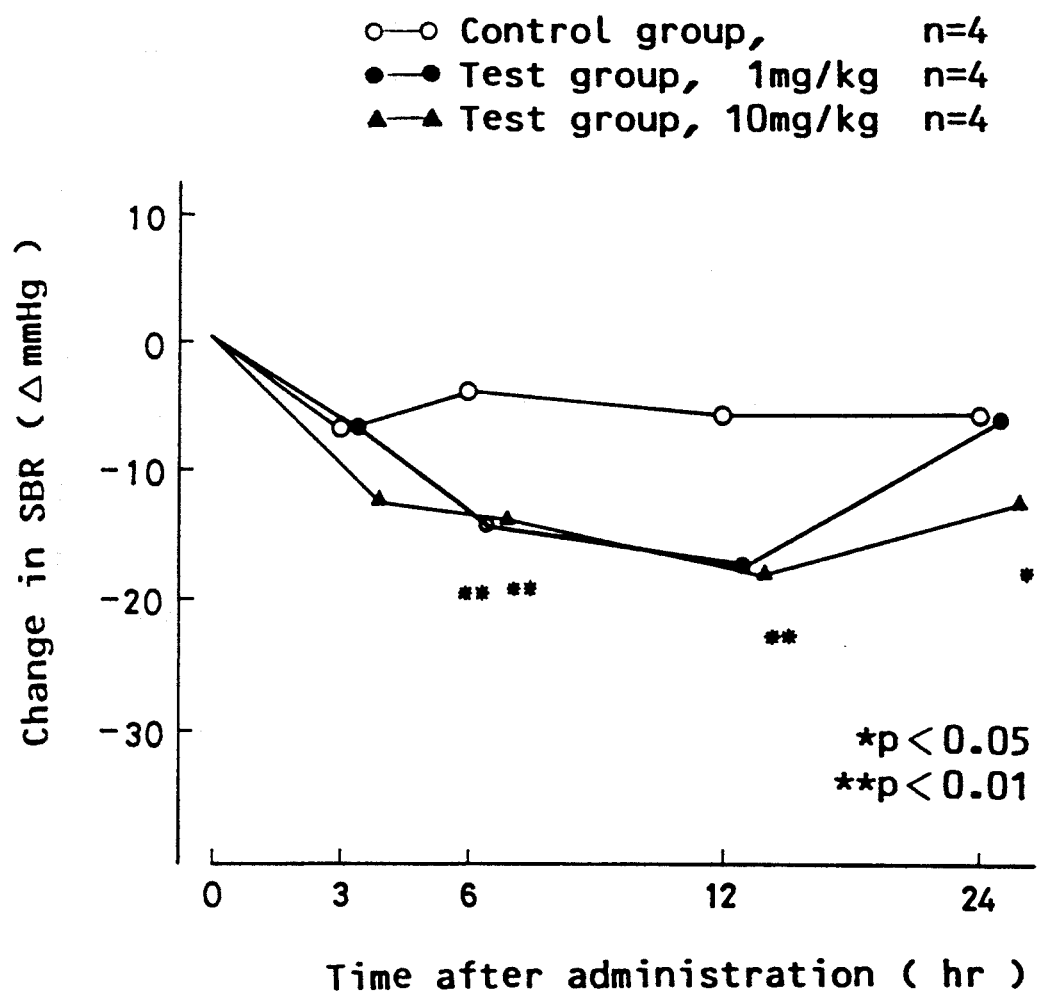
FIG. 5 is a diagram showing the results obtained by administrating polysaccharide-peptidoglycan complexes to SHR rats.

FIG. 5 is a diagram showing the results of oral administration of the polysaccharide-peptidoglycan complexes to SHR. As shown in FIG. 5, the group given the 1 mg/kg dose of polysaccharide-peptidoglycan complexes showed significant reduction in blood pressure 6 hours after administration, compared with that of the control group. Furthermore, the reduction in blood pressure was likely to be observed up to 12 hours later. Still more, significant blood-pressure reduction was observed in the group given the 10 mg/kg dose, continuously from 6 hours to 24 hours after the administration. No side effect of oral administration of the polysaccharide-peptidoglycan complexes on HR was observed.

EXAMPLE 2

Hypotensive action on renal hypertensive rats (1) Procedure

The left renal artery was detached from male Wistar rats (Crj-cd, body weight 160–190 g) under anesthesia with pentobarbital-Na (50 mg/kg, i.p.), and a silver clip of a 0.22 mm slit width, a 1.5 mm width, a 3 mm length and a 1 mm thickness was placed on the artery for inducing stenosis in the renal artery, to make hypertensive rats (2K1 clip rats).

When 4 weeks or more passed after the surgery, the rats showing SBP 170 mmHg or more were picked up and classified into three groups; 1 mg/kg dose group, 10 mg/kg dose group and 0.5 ml/100 g water group (control group).

For blood pressure measurement, rats unanesthetized were prewarmed at 38° C. for a few minutes to measure SBP at the caudal vein and the heart rate (HR), was determined using a programmable sphygmomanome: (PS100 manufactured by Riken Kaihatu, K.K.). Measurement was carried out before and 3, 6, 12 and 24 hours after the sample administration.

The change in SBP or HR before and after the administration was determined (the average reduction±S.D.) and was statistically examined compared with those changes in the control group, using a Student's t-test. The change, if the risk level 5% or more was observed, was defined statistically as significant.

(2) Results

Figure 6:
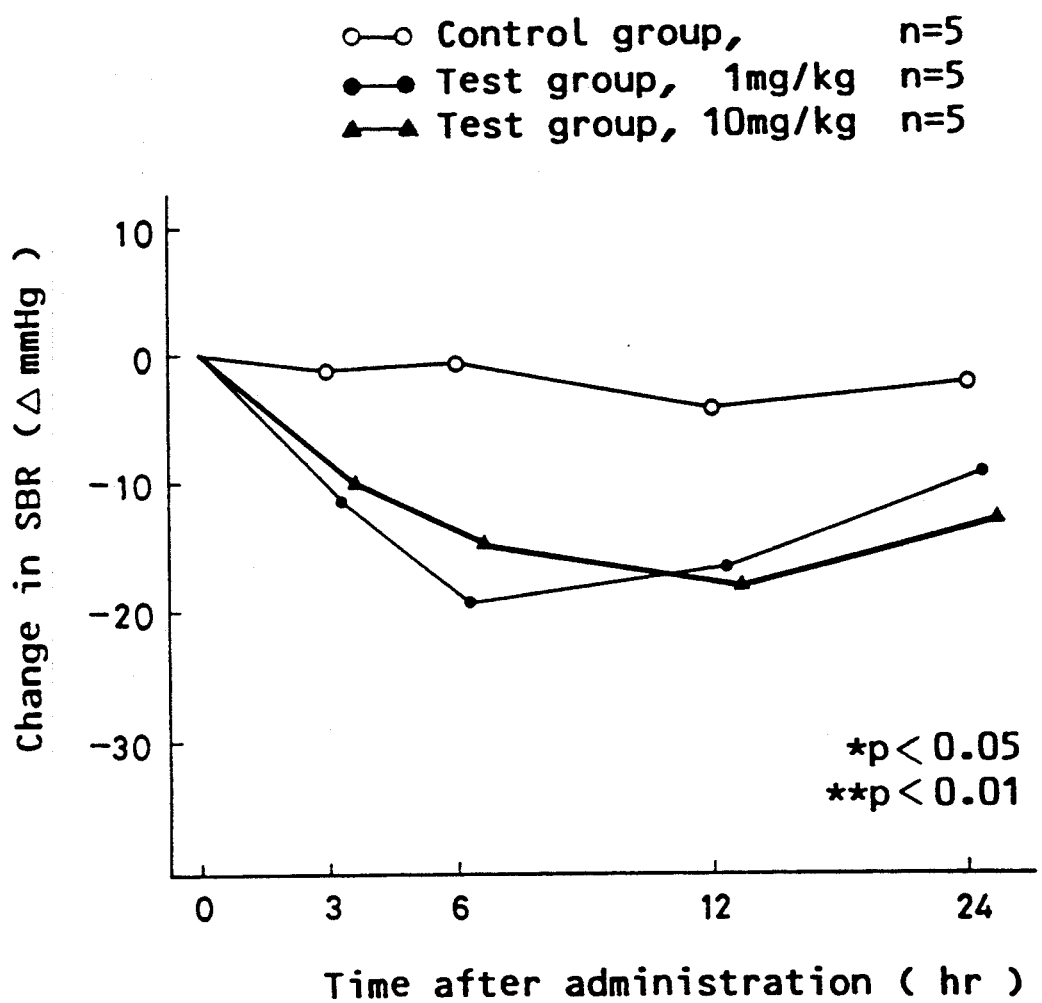
FIG. 6 is a diagram showing the results obtained by administering polysaccharide-peptidoglycan complexes to renal hypertensive rats.

FIG. 6 is a diagram showing the results of oral administration of the polysaccharide-peptidoglycan complexes to renal hypertensive rats. As shown in FIG. 6, the group given the 1 mg/kg dose of polysaccharide-peptidoglycan complexes showed significant reduction in blood pressure 3 hours up to 12 hours after the administration, compared with that of the control group. Furthermore, the reduction in blood pressure was likely to be observed up to 24 hours later. Still more, similar effects were observed in the group given the 10 mg/kg dose. No side effects of oral administration of the polysaccharide-peptidoglycan complexes on HR was observed.

Any route including oral, intraperitoneal and intravenous administration may be employed for administering the antihypertensives containing as effective component the polysaccharide-peptidoglycan of the present invention, but the oral administration may be preferable in order to ensure hypotensive effects more efficiently. A single dose thereof as low as 1–5 mg/kg may be sufficient. Starting about 2–3 hours after the dose, the blood pressure reduction over 10–30 mmHg is observed and the effect continues up to 12–24 hours or more after the dose. Continuous administration is still more effective and in that case, even the lesser dose may exert hypotensive effects.

The antihypertensives of the present invention have the following excellent features;

1. They are the antihypertensives originated from lactic acid bacteria, which are used in the production of the fermented milk food and drinks such as the yogurt.
2. They are the substances from natural origin which can exert hypotensive effects at a dose much less than the dose of the known polysaccharides produced by plants, sea weeds and microorganisms.
3. Since they are water soluble, they can be readily prepared in appropriate formulations.

In addition, they are extremely safe and can be administered continuously for a long period.

4. Food and drinks (1) Production of drinks

To commercially available 100% orange juice was added the water extract 6 g/1 l of the lactic acid bacterium cells produced in Production Example 1 (LEx; crude substance containing polysaccharide-glycopeptide complexes) (6 g/1 l) or the purified polysaccharide-peptidoglycan complexes (SG-1) 200 mg/1 l to produce drinks having hypotensive actions.

(2) Production of food

LEx 6 g/1 l or SG-1 200 mg/1 l was added to the commercially available fermented milk containing Lactobacillus or Bifidobacterium to produce a food having hypotensive actions.

(3) Hypotensive action

The hypotensive action of the food and drinks produced by the above steps (1) and (2), was observed in SHR and compared with the action of control orange juice and fermented milk without LEx and SG-1. The results are shown in Table 3.

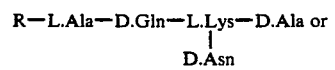

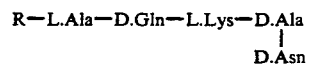

wherein
L—Ala is L-alanine,
D—Gln is D-glutamine,
L—Lys is L-lysine and
D—Asn is D-asparagine, and wherein R is polysaccharide

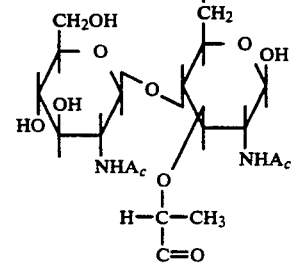

2. A food or drink composition having an antihypertensive action, containing as active ingredient, and antihypertensive amount of a polysaccharide-peptidoglycan complex extracted from the cell walls of lactic acid bacteria by hot water extraction, wherein the polysaccharide-peptidoglycan complex has one of the following amino acid sequences;

R—L.Ala—D.Gln—L.Lys—D.Ala,

TABLE 3

| Administered sample | Systolic blood pressure | | |
|---|---|---|---|
| | before administration | 6 hrs. later | 24 hrs. later |
| 100% orange juice (5 mg/kg) | 181.2 ± 1.1 | 175.9 ± 7.2 | 182.1 ± 2.5 |
| 100% orange juice + LEx (30 mg LEx/5 mg/kg) | 179.3 ± 1.5 | 164.8 ± 4.6** | 175.5 ± 6.4 |
| 100% orange juice + SG-1 (1 mg SG-1/5 mg/kg) | 182.0 ± 1.2 | 174.8 ± 4.1* | 175.5 ± 1.4*** |
| Fermented milk containing Bifidobacterium (5 mg/kg) | 179.8 ± 3.3 | 180.2 ± 1.9 | 181.4 ± 4.4 |
| Fermented milk containing Bifidobacterium + LEx (30 mg LEx/5 mg/kg) | 181.1 ± 0.4 | 171.2 ± 0.9*** | 175.7 ± 5.2 |
| Fermented milk containing Bifidobacterium + SG-1 (1 mg/5 mg/kg) | 180.8 ± 1.5 | 167.7 ± 3.7*** | 177.5 ± 4.2 |

(In the table, *represents P < 0.05; P < 0.01; *P < 0.001.)

Table 3 shows that food and drinks capable of decreasing systolic blood pressure may be available by adding LEx or SG-1 to general food and drinks.

What is claimed is:

1. An antihypertensive containing, as an active ingredient, an antihypertensive effective amount of a polysaccharide-peptidoglycan complex extracted from the cell walls of lactic acid bacteria by water extraction, wherein the polysaccharide-peptidoglycan complex has one of the following amino acid sequences;

R—L.Ala—D.Gln—L.Lys—D.Ala,

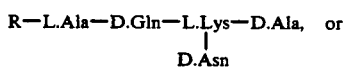

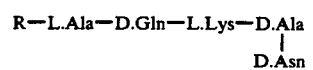

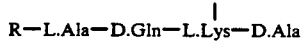

wherein each abbreviation in the formulae means the following amino acid respectively, L-Ala is L-alanine, -continued
D-Gln is D-glutamine,
L-Lys is L-lysine, and
D-Asn is D-asparagine,
-continued
wherein R is polysaccharide
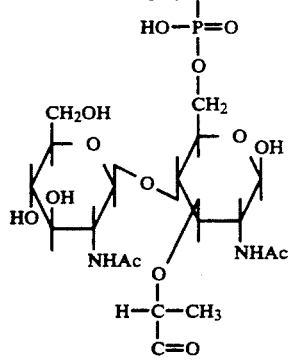
* * * * *